United States Patent [19]

McIntyre

[11] 4,247,380

[45] Jan. 27, 1981

[54] TECHNIQUE FOR IN SITU CALIBRATION OF A GAS DETECTOR

[75] Inventor: William H. McIntyre, Orrville, Ohio

[73] Assignee: Westinghouse Electric Corp., Pittsburgh, Pa.

[21] Appl. No.: 616,712

[22] Filed: Sep. 25, 1975

[51] Int. Cl.³ ............................................. G01N 27/46
[52] U.S. Cl. .................................. 204/195 S; 204/1 T
[58] Field of Search .................... 204/1 S, 195 S, 1 T, 204/195 R; 73/1 G

[56] References Cited

U.S. PATENT DOCUMENTS

| | | | |
|---|---|---|---|
| 3,223,608 | 12/1965 | Hersch | 204/195 R |
| 3,546,086 | 12/1970 | Sayles | 204/195 S |
| 3,597,345 | 8/1971 | Hickam et al. | 204/195 S |
| 3,598,711 | 8/1971 | Flais | 204/195 S |
| 3,699,032 | 10/1972 | Rapp | 204/195 S |
| 3,791,937 | 2/1974 | Besson et al. | 204/1 S |
| 3,835,012 | 9/1974 | Hemak | 204/195 S |
| 3,838,021 | 9/1974 | Arbiter | 204/195 S |
| 3,909,385 | 9/1975 | Spielberg et al. | 204/195 S |
| 3,915,828 | 10/1975 | Cleary et al. | 204/195 S |
| 3,928,161 | 12/1975 | McIntyre et al. | 204/195 S |
| 3,948,604 | 4/1976 | Hoppesch | 73/1 G |

*Primary Examiner*—T. Tung
*Attorney, Agent, or Firm*—M. P. Lynch

[57] ABSTRACT

In a gas measuring probe assembly having a gas sensing device within a tubular housing positioned within a gas environment to be monitored, a tubular calibration gas flow pattern is established within the tubular housing substantially parallel to the walls of the tubular housing to sweep the monitored gas environment from the tubular housing and expose the gas sensing device to a calibration gas mixture substantially free of the monitored gas environment. This technique permits the in situ calibration of gas detectors, and is especially useful in calibrating stack gas monitoring probes.

2 Claims, 10 Drawing Figures

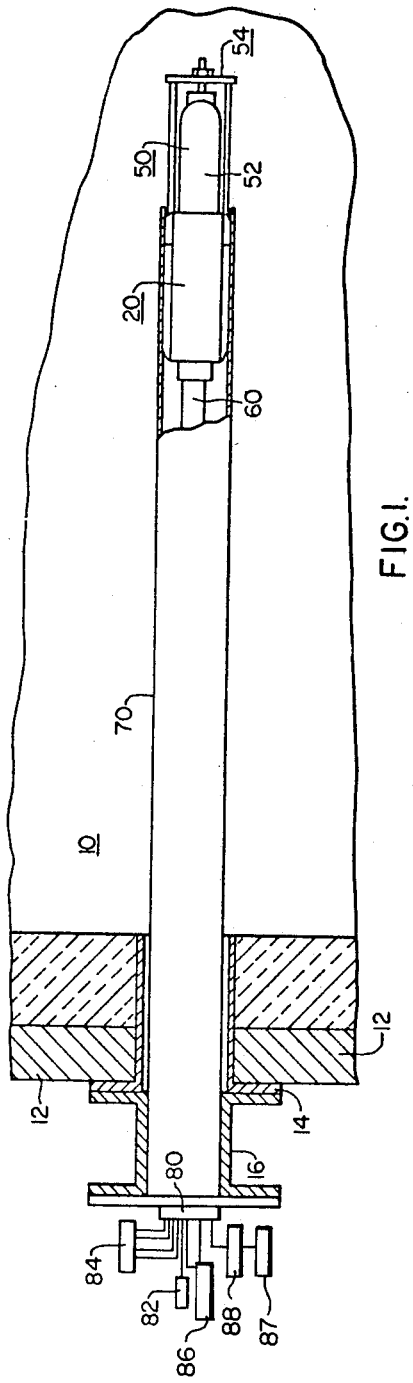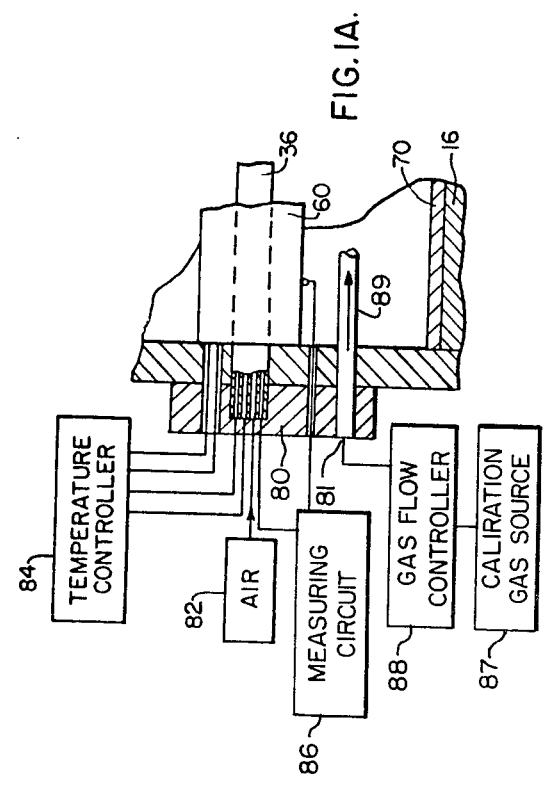

TECHNIQUE FOR IN SITU CALIBRATION OF A GAS DETECTOR

BACKGROUND OF THE INVENTION

The requirement for removing gas detectors from heated, corrosive industrial environments for the purposes of periodic calibration of the gas sensing device is a disadvantage associated with conventional in situ gas probes of the type described in copending patent application Ser. No. 247,368, entitled "Improved Gas Measuring Probe For Industrial Applications", filed Apr. 25, 1972, now abandoned and U.S. Pat. No. 3,928,161, entitled "Improved Gas Measuring Probe For Industrial Applications", issued Dec. 23, 1975 the latter being a divisional application of the former, and both being assigned to the assignee of the present invention.

The tedious task of removing a gas detector from a heated and sometimes dangerous environment, coupled with the loss of the probe as an in situ gas monitoring device during the remote calibration activity clearly identifies a need for a practical technique to permit in situ calibration of gas detectors.

SUMMARY OF THE INVENTION

There is disclosed herein with reference to the accompanying drawings an in situ calibration technique for application to a gas detector having an open ended tubular housing and a gas sensing device positioned within the tubular housing and spaced apart from the walls of the tubular housing to monitor gas constituents of a monitored gas environment entering one end of a tubular housing. At the opposite end of the tubular housing, there is a gas flow director connected to source of calibration gas, which directs a tubular calibration gas flow pattern through the tubular housing to the end of the tubular housing which is exposed to the monitored gas environment. The tubular calibration gas flow pattern, which is coaxially disposed within the tubular housing, effectively sweeps the monitored gas environment from within the tubular housing through the open end of the tubular housing such that the signal developed by the gas sensing device is a measurement of the calibration gas. The tubular calibration gas flow pattern prevents mixing of the calibration gas with the monitored gas at the gas sensing device thus reducing erroneous calibration measurements and providing a fast and effective technique for calibrating the gas sensing device without removing the gas probe assembly from its in situ location.

DESCRIPTION OF THE DRAWINGS

The invention will become more readily apparent from the following exemplary description in connection with the accompany drawings:

FIG. 1 is a schematic illustration of a gas probe assembly of the type described in the above referenced copending applications but further including an in situ gas calibration apparatus;

FIG. 1A is a partial sectioned view of FIG. 1 detailing the interconnect arrangement for incorporating an in situ gas calibration apparatus in a gas analyzer probe assembly;

DESCRIPTION OF THE PREFERRED EMBODIMENT

Figure 2:
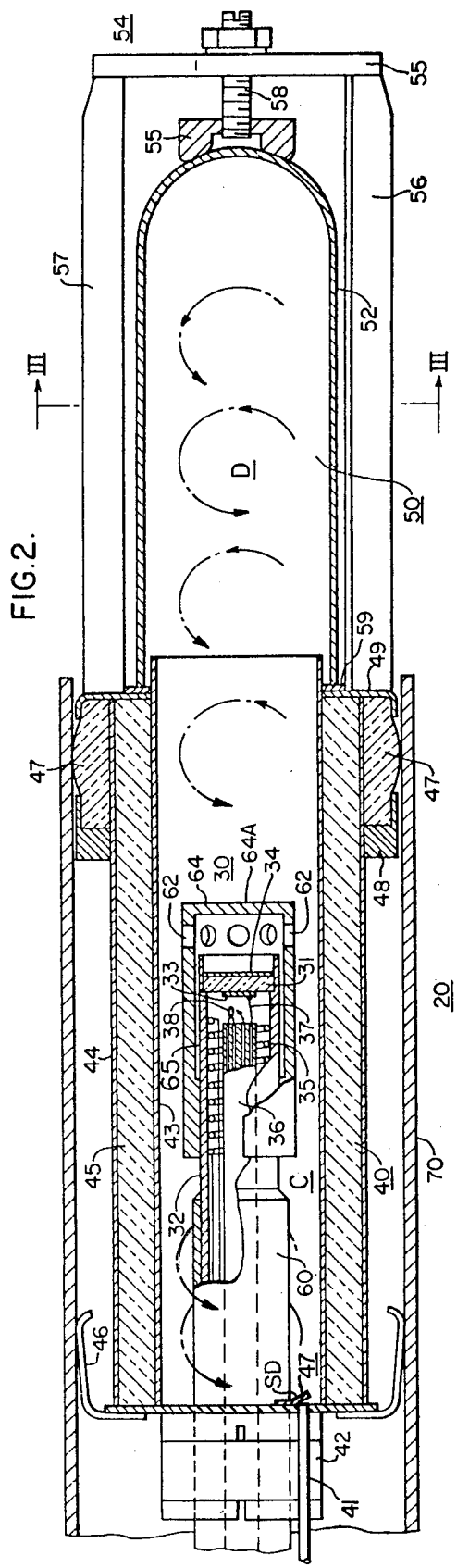
FIG. 2 is a detailed section schematic illustration of the gas probe assembly of FIG. 1 depicting the gas director included within the gas sensor tubular housing to effect the tubular gas flow pattern of the calibration gas within the tubular housing.

Referring to FIG. 1, there is illustrated a typical embodiment of a solid electrolyte oxygen probe assembly 10 inserted within the wall 12 of a furnace F to monitor the oxygen content of the furnace environment. The furnace F is provided with an insertion flange 14 providing entry from outside the wall 12 into the furnace environment. The probe assembly 10 is secured to the furnace flange 14 by means of flange 16. The probe assembly 10 is comprised of solid electrolyte oxygen sensor assembly 20, porous protective shield 50 and tubular extension member 60 for positioning the combination of the oxygen sensor assembly 20 and protective shield 50 within the stationary tubular support member 70. Supporting apparatus for the operation of the solid electrolyte oxygen cell assembly 20 is typically illustrated in U.S. Pat. No. 3,546,086, entitled Device For Oxygen Measurement, issued Dec. 8, 1970 and assigned to the assignee of the present invention. This includes an interconnect assembly 80 for supplying oxygen reference gas from reference gas source 82 to the cell assembly 20 as well as providing signal leads for a temperature sensing element in the cell assembly 20 for monitoring cell temperature by temperature controller 84. The electrical signal developed by the solid electrolyte electrochemical cell assembly 20 in response to the oxygen content of the furnace environment is transmitted to the EMF measuring or recording apparatus 86 through the interconnect assembly 80. While the signal developed by the cell assembly 20 is indicated as being utilized for record or measurement purposes, it is equally applicable for use as a feedback signal to control a combustion apparatus as illustrated in U.S. Pat. No. 3,404,836, entitled Heat Generating Apparatus, and issued Oct. 8, 1968. The scheme of interconnections of the probe assembly 10 with units 82, 84 and 86 is illustrated in FIG. 1A.

The interconnect assembly 80 further includes a passage 81 to accommodate the flow of calibration gas from the calibration gas source 87 which is regulated by gas flow controller 88. The calibration gas passes through a gas entry tube 89 which extends through aperture 41 in the interconnect member 42. The calibration gas introduced into the housing chamber C from the gas passage 41 contacts a gas director 47 which diverts the flow of calibration gas into a tubular calibration gas flow pattern as illustrated by the arrows. The advantages of thwe tubular calibration gas flow pattern produced by the gas director 47 as a device for permitting in situ calibration of oxygen sensor assembly 20 will be discussed in detail with reference to FIGS. 4-9.

There is illustrated in FIG. 2 a sectioned schematic representation of the combination of the solid electrolyte oxygen sensor assembly 20 and the protective shield assembly 50. The oxygen sensor assembly 20 is comprised of solid electrolyte cell assembly 30 which is secured to the tubular extension member 60 and which in turn is fixedly secured within a tubular insulating member 40 by the interconnect member 42. The tubular thermal insulating member 40 is in the form of a tubular can typically constructed of inner and outer walls 43 and 44 within which is packed a thermal insulating material 45 which functions to effectively insulate the temperature sensitive oxygen solid electrolyte cell assembly 30 from heat transfer from the temperature environment existing within the furnace environment. Attached to the tubular member 40 are spring members 46 which in conjunction with the cylindrical sealing collar 47 function to stably align and position the combination of the oxygen sensor assembly 20 and the protective shield assembly 50 within the stationary tubular member 70. The sealing collar 47 which is in the form of a collar positioned about the tubular thermal insulating member 40 is illustrated as comprised of the same thermal insulating material utilized within the walls of the tubular thermal insulating member 40 and provides an effective diameter sufficient to provide essentially a force-fit of the combination of assemblies 20 and 50 within the tubular member 70. The sealing collar 47, in addition to providing alignment of the assembly combination, also serves to provide a barrier whereby particles in the furnace environement are prevented from traveling within the tubular member 70, thus avoiding a build-up of foreign matter which could adversely affect the insertion and removal of the probe assembly 10. The thermal insulating material utilized within the tubular thermal protection device 40 and used as the sealing collar 47 can be one of many thermal insulating materials available including Fiberfrax insulation, which is a product of the Carborundum Company. The effective diameter of the sealing collar 47 can be varied by the positioning of the adjustable clamp 48.

The solid electrolyte cell assembly 30 is comprised of a solid electrolyte member 31 illustrated in the form of a disc sealed to form the closed end of tubular support member 32 which has the opposite end secured to the tubular extension member 60. Disposed on opposite surfaces of the solid electrolyte member 31 are electrode members 33 and 34. The material composition of the solid electrolyte can be satisfied by any of many compositions of materials well known in the art which support oxygen ion conductivity. Such material compositions are described in U.S. Pat. No. 3,400,054 issued Sept. 3, 1968. A requirement for the electrode members 33 and 34 is that they provide sufficient electronic conductivity and operable at elevated temperatures. The prior art typically represents the electrodes as being porous platinum coatings. In selecting the material for the tubular support member 32 for an oxygen probe assembly for use in industrial applications, the prime considerations are the material's resistance to corrosion and a need to match as closely as possible the thermal coefficient of expansion of the tubular material with that of the solid electrolyte. Materials satisfying these requirements include 446 Stainless, Ebrite 26-1, Hastelloy B, Inconel X, etc. Investigations have shown that the Ebrite 26-1 provides characteristics compatible with conventional solid electrolyte material composition to satisfy the requirements of corrosion resistance and matching coefficients of thermal expansion to insure an integral seal between the solid electrolyte member 31 and the tubular support member 32.

A heater assembly 35 positioned within the tubular support member 32 provides uniform operating temperature for the solid electrolyte cell assembly. Electrical leads 35A from the heater assembly 35 extend within tubular member 60, through interconnect member 80 to temperature controller 84.

Entry tube 36 extending from the interconnect member 80 of FIG. 1 includes at least four longitudinal passages therein whereby an electrical lead member 37 is brought in contact with electrode 32 and leads for temperature measuring element 38 are carried to the temperature controller 84 to provide input information for controlling the operation of the heater assembly 35. The fourth longitudinal passage in the entry tube 36 permits the passage of a reference oxygen supply, such as air, exhibiting a known oxygen content from the reference gas supply 82 to the surface of the solid electrolyte member 31 occupied by the electrode 33 and exhausted back through interconnect member 80.

A suitable composition for the solid electrolyte 31 includes a composition of Zirconia and oxides of calcium or related material which provides sufficient oxygen ion conduction to render the solid electrolyte useful for oxygen gas measurement.

The use of electrically conductive material for the tubular support member 32 permits the extension of the electrode member 34 to electrical contact with the tubular member 32 thus permitting the use of the tubular member 32 as an electrical conductor to conduct the signal developed by the solid electrolyte member in response to oxygen differential pressure. The use of a metal material for the tubular extension member provides additional conduction of the signal to the interconnect member 80 at which electrical contact is made by a lead extending to the signal measuring circuit 86.

As described in the reference U.S. Patents, the operation of the conventional solid electrolyte oxygen cell is such that the electrolyte member 31 will respond to a difference in oxygen pressure between that of the oxygen reference present at electrode 33 and that of the environment present at electrode 34 by generating an EMF signal which is monitored by the remote measuring apparatus 86 and interpreted as a measurement of the oxygen content of the unknown environment present at electrode 34. In the instant application, the environment present at the electrode 34 corresponds to the furnace environment which is conducted through the porous protective shield member 52 of the protective shield assembly 50 by diffusion and is introduced to the surface of the solid electrolyte member 31 upon which electrode 34 is disposed through apertures 62 in a heat-conductive cap 64. The construction and the operation of the solid electrolyte member 31 in conjunction with electrodes 33 and 34 in response to varying oxygen environments is clearly described in the referenced patents and will therefore not be described in detail in this application.

The heat conductive cap 64 serves primarily to conduct heat produced by the heater assembly 35 to the end cap portion 64A of the heat conductive cap 64. The end cap 64A serves as a stable temperature barrier whereby the volume V is maintained at a relatively stable temperature corresponding to that required for the desired operation of the oxygen cell assembly. An annular air space 65 is included to serve as an insulating barrier which essentially eliminates "short circuit" of the thermal conduction from the heat conductive cap to the solid electrolyte 31 through the tubular support member 32 and assures conduction of the heat to the closed end portion 64A. Of secondary importance, is the mechanical protection provided the relatively fragil solid electrolyte 31 by the closed end heat conductive cap during handling of the oxygen sensor assembly prior to insertion within the furnace environment. The heat conductive cap can be fabricated from any suitable material exhibiting the thermal conduction characteristics required, such as, 304 Stainless Steel, 446 Stainless Steel, Ebrite 26-1, etc.

The protective shield assembly 50 includes a mechanical support structure 54 which is fixedly secured to end piece 49 of the open ended tubular insulating member 40. The mechanical structure 54 includes end plate 55 and leg members 56 and 57 extending between the end plate 55 and the end piece 49. An adjustable clamping assembly 58 associated with the end plate 55 serves to apply controlled force against the closed end of the tubular porous member 52 to effectively seal the open end of the tubular porous member 52 against sealing member 59. The sealed positioning of the open end of the tubular porous member 52 against the sealing member 59 effectively isolates the oxygen sensor assembly 30 from contact by foreign matter present in the furnace environment. The use of a material which will readily support oxygen diffusion at elevated temperatures for the porous member 52 assures the sensitivity of the oxygen sensor assembly to the oxygen content of the furnace environment. The requirements for selecting a material exhibiting desirable mechanical characterics suitable to enable the porous member to withstand impingement by foreign matter while at the same time providing rapid gas diffusion can be satisfied by selecting a porous refractory material such as a ceramic material or a metal having a porosity sufficient to prevent passage of dust and particulate matter while permitting the desired level of gas diffusion. A commercially available porous refractory material in the form of an extraction thimble produced and marketed by Fisher Scientific satisfies the requirement of the porous member 52.

Figure 3:
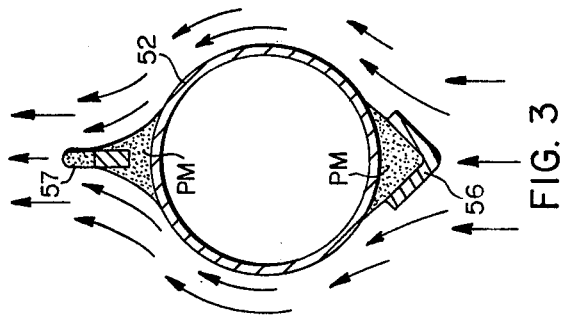
FIG. 3 is a section view III—III of the probe assembly of FIG. 2 illustrating a typical gas flow pattern established by an externally mounted gas flow deflector.

Referring to FIG. 3, there is illustrated a section of the embodiment of FIG. 2 illustrating the position and configuration of the leg members 56 and 57 of the mechanical support structure 54 and the orientation of the leg members relative to the gas flow within the furnace environment. The configuration of the leg member 56 is such as to form a deflecting member resulting in an external gas flow pattern as illustrated. The deflector configuration of the leg member 56 serves two purposes:

a. prevents direct impingement of large particulate matter on the surface of the porous member 52;

b. establishes a sweeping air flow across the outside surfaces S1 and S2 of the porous member 52 to effectively provide a wiping or cleaning action, thus eliminating a build-up of particulate matter on the surfaces S1 and S2 of the porous member 52 which could ultimately seal the pores of the member 52 thus preventing rapid diffusion of oxygen gas therethrough.

Field tests of the configuration illustrated in FIG. 3 resulted in a build-up of particulate matter PM as illustrated. While the deflector configuration of the leg member 56 is simply illustrated as a right angle member, it is apparent that numerous configurations are available to provide the desired gas flow patttern.

Referring once again to the in situ calibration capability provided by the calibration gas source 87, the gas flow controller 88, the calibration gas entry tube 89 and the gas director 47, it is noted that the in situ calibration capability not only eliminates the need for removal of the probe assembly 10 from the wall 12 but also permits the utilization of the heater assembly 35 for maintaining the desired gas sensor operating temperature and the measuring circuit 86 for monitoring calibration data. Furthermore, the fact that the probe assembly 10 is maintained in its intended operating environment i.e. the furnace stack, the calibration information will be more authentic in that it will reflect the dynamic conditions of the operating environment, i.e. temperature gradients along the probe assembly 10.

Figure 9:
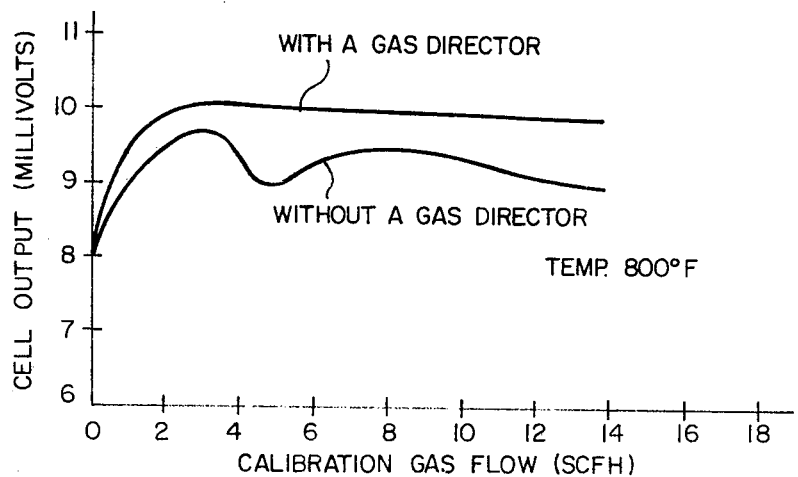
FIG. 9 is a graphical illustration effect of the gas directors of FIGS. 2, 4-8 on calibration gas flow.

The tubular calibration gas flow pattern illustrated by the arrows effectively flushes the monitored gas environment contained from within the volumes C and D through the porous filter member 52. This is graphically illustrated in FIG. 9. The tubular calibration gas flow pattern also establishes a boundary condition at the exterior surface of the filter member 52 to prevent the inward diffusion of stack gases during the calibration of the oxygen sensor assembly 20. The gas flow controller 88 assures a continuous tubular wall of calibration gas in accordance with the flow pattern illustrated by the arrows so as to assure substantially complete flushing of the stack gas from the volume C such that the electrical signals monitored by the measuring circuit 86 indicate the response of the oxygen sensor assembly 20 to the calibration gas as shown in FIG. 9. Following a reading indicative of a first calibration gas, a second calibration gas exhibiting a different predetermined oxygen content, can be introduced into chambers C and D to provide a second electrical measurement corresponding to a second point on a calibration curve. Additional calibration gas samples, each of a predetermined oxygen content may be subsequently introduced in the same manner with the resulting electrical signals monitored by the measuring circuit providing data points from which a complete calibration curve may be plotted.

Experimental evaluation of numerous designs of gas directors for producing a tubular calibration gas flow pattern clearly indicate that the tubular calibration gas flow pattern provides the necessary rapid flushing of the furnace stack gases from the internal volumes C and D without mixing with the monitored gas environment in volume C so as to provide a rapid, reliable indication of the response of the oxygen sensor assembly 20 to a calibration gas exhibiting a predetermined oxygen content.

Referring to FIG. 2, the gas director 47 is illustrated as consisting of a spiral gas deflector SD extending over the exit aperture of the gas passage 41 of the calibration gas entry tube 89. The gas deflector SD includes a gas deflector surface S angularly disposed so as to direct the calibration gas entering the volume C into a spiral tubular gas flow pattern which spirals upward through volumes C and D to form a tubular gas flow pattern coaxially disposed about the longitudinal axis of the probe assembly 10. This tubular gas flow pattern, which can be considered as forming a "tube" having an inside diameter approximating the diameter of the end portion 64A of the 64 and an outside diameter corresponding substantially to the inside diameters of the insulating member 40 and the tubular porous member 52, and extending through volumes C and D of the probe assembly 10.

Figure 5:
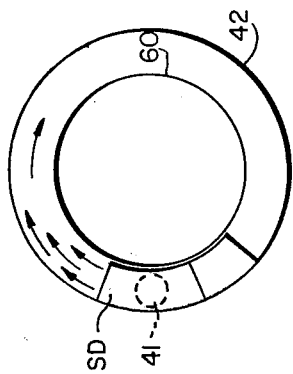
FIGS. 4-8 are detailed illustrations of various gas director designs for effecting the tubular calibration gas flow pattern.
Figure 4:
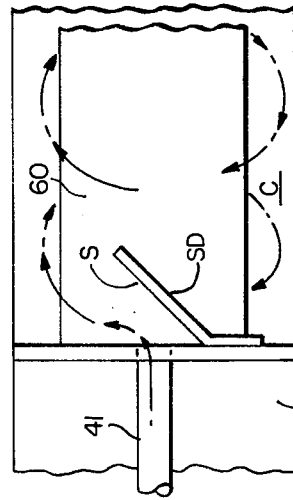

The spiral gas deflector SD of FIG. 2 and the corresponding spiral tubular gas flow patterns are illustrated in detail in FIGS. 4 and 5.

Figure 6A:
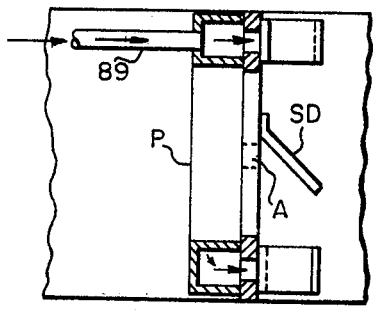
Figure 6B:
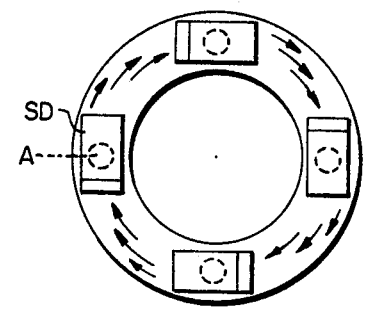
Figure 7:
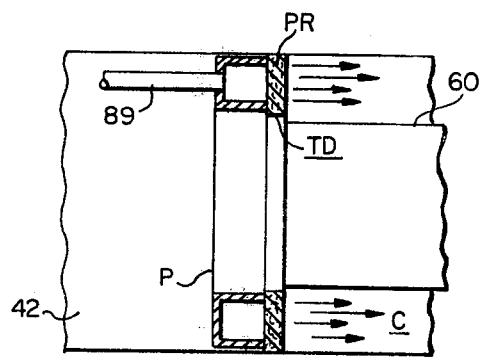
Figure 8:
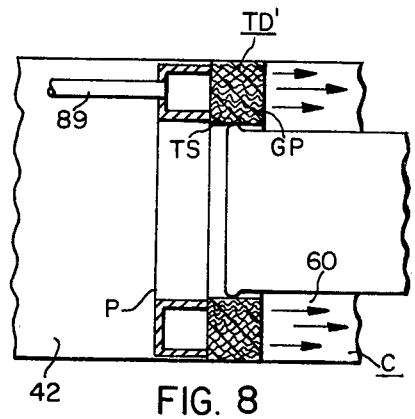

A variation of the gas director 47 of the type illustrated in FIGS. 2, 4 and 5 for producing a spiral tubular gas flow pattern is illustrated in FIGS. 6A and 6B. In this configuration, an annular gas passage P directs the calibration gas from the gas entry tube 89 through a plurality of apertures A with which there are associated corresponding spiral gas deflectors SD. The gas director configuration of FIGS. 6A and 6B assures a continuous, unbroken wall of calibration gas forming the desired tubular gas flow pattern. Alternatives to the use of spiral gas deflectors SD to form a suitable calibration gas director 47 to produce the desired tubular calibration gas flow pattern are illustrated in FIGS. 7 and 8. The gas director configurations illustrated in FIGS. 7 and 8 establish a translation gas flow pattern as illustrated by the arrows in contrast to the spiral gas flow pattern of the gas director configuration of FIGS. 2, 4, 5, 6A and 6B.

In the gas director configuration of FIGS. 7 and 8, an annular gas passage P, similar to that illustrated in FIGS. 6A and 6B, is provided to direct calibration gas from the calibration gas entry tube 89 through an annular translational gas director TD and TD', respectively. The annular translational gas director TD of FIG. 7 as illustrated as consisting of a porous ring PR while the translational gas director TD' of FIG. 7 is illustrated as consisting of a plurality of thin tubular sleeves TS forming a collar C having annular gas passages GP corresponding to the spacing between adjacent tubular sleeves. The translational tubular gas flow pattern established by the configurations of FIGS. 7 and 8 produce the unbroken wall of calibration gas required to flush the chambers C and D of the monitored gas environment introduced through the porous filter member 52 while eliminating continuous mixing of the calibration gas with the monitored gas environment at the sensitive surface of the solid electrolyte cell assembly 30 corresponding to the electrode member 34. The rapid flushing of the monitored gas environment from the volumes C and D by the turbulent or laminar flow of the tubular calibration gas flow pattern quickly renders the solid electrolyte cell assembly 30 responsive solely to the calibration gas as illustrated in FIG. 9.

The monitored gas present within cap 64 and adjacent to electrode 34 is removed rapidly through apertures 62 either by turbulent mixing or by diffusion between the monitored gas and calibration gas until equilibrium is reached.

The use of the gas flow controller 88 for supplying the calibration gas to the gas director 47 renders the flow of the calibration gas relatively independent of the back pressure encountered in the normal range of pressures of monitored gas environments. A very low differential pressure exists across the porous filter member 52 under wide changes in gas flow rate. Thus the pressure variations encountered at the solid electrolyte electrochemical cell assembly 30 are limited to less than 0.1 inches of water with calibration gas flow rates of up to 12 SCFH. This results in a variation in the electrical output signal of the solid electrolyte cell assembly 30 of less than 0.0001 per unit output for variations due to the difference between the gas pressure within volume C and the gas pressure in the monitored environment external to the filter member 52. At low calibration gas slow rates, i.e. less thaan 5 SCFH, back diffusion of the monitored gas through filter 52 has been observed.

I claim:

1. In a gas measuring probe assembly having a solid electrolyte gas sensing device located within a tubular housing to generate electrical signals indicative of the gas constituents of a monitored gas entering the tubular housing, the combination of, a calibration gas director means including a calibration gas manifold ring positioned within said tubular housing and having apertures therein, means for introducing calibration gas into said calibration gas manifold ring, said calibration gas manifold ring directing calibration gas flow through said apertures to produce a tubular calibration gas flow pattern within said tubular housing to sweep said monitored gas from said solid electrolyte gas sensing device and expose said solid electrolyte gas sensing device to said calibration gas, said solid electrolyte gas sensing device generating an electrical signal in response to said calibration gas.

2. In a gas measuring probe assembly having a solid electrolyte gas sensing device located within a tubular housing to generate electrical signals indicative of the gas constituents of a monitored gas entering the tubular housing, the combination of, a calibration gas director means including a porous ring member and means for directing calibration gas through said porous ring member to develop a tubular calibration gas flow pattern within said tubular housing to sweep said monitored gas from said solid electrolyte gas sensing device and expose said solid electrolyte gas sensing device to said calibration gas, said solid electrolyte gas sensing device generating an electrical signal in response to said calibration gas.

* * * * *